United States Patent [19]

O'Neil

[11] Patent Number: 5,032,300
[45] Date of Patent: Jul. 16, 1991

[54] LUBRICANT COMPOSITION

[75] Inventor: Robert M. O'Neil, Manchester, England

[73] Assignee: Ciba-Geigy Corporation, Ardsley, N.Y.

[21] Appl. No.: 420,205

[22] Filed: Oct. 12, 1989

[30] Foreign Application Priority Data

Oct. 18, 1988 [GB] United Kingdom ............... 8824402

[51] Int. Cl.$^5$ .......................................... C10M 133/44
[52] U.S. Cl. ............................................... 252/51.5 R
[58] Field of Search ........................... 252/51, 51.5 R

[56] References Cited

U.S. PATENT DOCUMENTS

| | | | |
|---|---|---|---|
| 4,107,060 | 8/1978 | Schick | 252/51.5 R |
| 4,153,565 | 5/1979 | Braid | 252/51.5 R |
| 4,174,285 | 11/1979 | Braid | 252/51.5 R |
| 4,260,501 | 4/1981 | Shim | 252/47.5 |
| 4,278,553 | 7/1981 | Sung | 252/51.5 R |
| 4,758,363 | 7/1988 | Sung et al. | 252/51.5 R |
| 4,824,601 | 4/1989 | Franklin | 252/401 |

FOREIGN PATENT DOCUMENTS

| | | | |
|---|---|---|---|
| 0149422 | 7/1985 | European Pat. Off. | |
| 0132005 | 11/1978 | Japan | 252/51.5 R |
| 2002772 | 2/1979 | United Kingdom | |

OTHER PUBLICATIONS

Derwent Abst. of EP 149,422.
Katritzky, J. Chem. Soc. Perkin Trans. I. 1987, p. 791.

Primary Examiner—Prince E. Willis
Assistant Examiner—Jerry D. Johnson
Attorney, Agent, or Firm—Stephen V. O'Brien

[57] ABSTRACT

The present invention provides lubricant compositions comprising a lubricant base and, as metal deactivator and/or antioxidant, at least one compound having the formula (I):

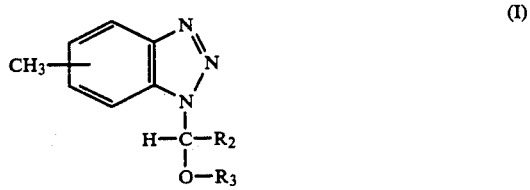

wherein
$R_2$ is $C_1$–$C_{12}$ straight or branched chain alkyl; and
$R_3$ is $C_1$–$C_{12}$ straight or branched chain alkyl interrupted by one or more O-atoms or $R_3$ is $C_5$–$C_{12}$ cycloalkyl.

10 Claims, No Drawings

LUBRICANT COMPOSITION

The present invention relates to lubricant compositions containing benzotriazole derivatives.

In British Patent Specification No. 2002772, there are described compounds, useful as metal deactivators in lubricants, and having the formula:

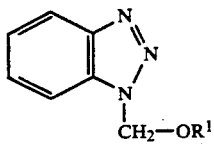

wherein $R^1$ is 1-18C alkyl, 3-18C alkenyl, 5-12C cycloalkyl or 6-10C aryl, each optionally substituted with one or more 1-12C alkyl or 7-9C aralkyl groups.

U.S. Pat. No. 4,153,565 discloses lubricant compositions containing, as antioxidants and corrosion inhibitors, the adduct of i) benzotriazole, optionally ring-substituted with a 1-12C hydrocarbyl group, and ii) an alkyl vinyl ether or a vinyl ester of a hydroxycarbylcarboxylic acid of formula

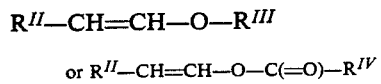

in which $R^{II}$ is hydrogen or a 1-18C alkyl group, $R^{III}$ is 1-18C alkyl and $R^{IV}$ is alkyl, aryl, alkaryl or aralkyl containing 1-18C-atoms.

Also known in U.S. Pat. No. 4,260,501 are lubricant compositions comprising the adducts of U.S. Pat. No. 4,153,565 together with an alkyl dimercapto thiadiazole, especially tertiary octyl 2,5-dimercapto-1,3,4-thiadiazole.

We have now found that certain N-substituted benzotriazoles provide improved metal deactivating and antioxidant properties when incorporated into lubricants.

Accordingly, the present invention provides lubricating compositions comprising a lubricant base and, as metal deactivator and/or antioxidant, at least one compound having the formula (I):

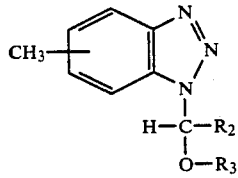

wherein
$R_2$ is $C_1$-$C_{12}$ straight or branched chain alkyl; and
$R_3$ is $C_1$-$C_{12}$ straight or branched chain alkyl interrupted by one or more O-atoms or is $C_5$-$C_{12}$ cycloalkyl.

$C_1$-$C_{12}$ alkyl groups $R_2$ include, e.g., methyl, ethyl, n-propyl, isopropyl, n-butyl, sec.-butyl, tert.-butyl, n-pentyl, n-hexyl, n-heptyl, n-octyl, 2-ethylhexyl, n-nonyl, 3,5,5-trimethylhexyl, n-decyl, n-undecyl or n-dodecyl.

$C_1$-$C_{12}$ alkyl groups $R_3$ interrupted by one or more, preferably by one to three, O-atoms include, e.g., $C_1$-$C_4$alkoxy-$C_1$-$C_4$-alkyl such as methoxymethyl, ethoxymethyl, 2-methoxyethyl, 2-ethoxyethyl, 3-methoxypropyl or 1- or 2-methoxybutyl; $C_1$-$C_4$ alkoxy-$C_2$-$C_4$-alkoxy-$C_1$-$C_4$alkyl such as 2-methoxyethoxymethyl; or di-$C_1$-$C_4$alkoxy-$C_1$-$C_3$alkyl e.g. dimethoxymethyl, diethoxymethyl, dipropyloxymethyl, 1,1- or 2,2-diethoxyethyl or 3,3-dimethoxypropyl.

When $R_3$ is $C_5$-$C_{12}$cycloalkyl, it may be e.g. cyclopentyl, cyclohexyl, cycloheptyl, cyclooctyl, cyclodecyl or cyclododecyl, especially cyclopentyl, cyclohexyl, cycloheptyl and cyclooctyl.

Preferred compounds of formula I are those wherein $R_2$ is $C_1$-$C_4$alkyl, and $R_3$ is $C_1$-$C_5$alkyl interrupted by one or two O-atoms or is $C_5$-$C_8$cycloalkyl. Especially preferred are compounds of formula I wherein $R_2$ is i- or n-propyl. Other especially preferred compounds of formula I are those wherein $R_3$ is a group of formula —$(CH_2CH_2O)_2CH_3$ or is $C_5$-$C_8$cycloalkyl.

It will be appreciated that the compounds of formula I may also exist in the isomeric form having the formula (IA):

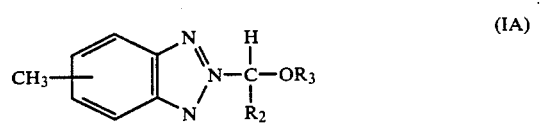

wherein $R_2$ and $R_3$ have their previous significance.

The compounds of formula I are known as a class, having been described by Katritzky et al. J. Chem. Soc. Perkin Trans 1 1987 p. 791-7.

Thus, Katritzky et al. describe adducts of benzotriazole and aldehydes having the formula (II):

wherein R is hydrogen, alkyl or aryl, e.g. methyl, ethyl, propyl, isopropyl, butyl, t-butyl, $(CH_2)_5CH_3$ or $(CH_2)_7CH_3$.

Katritzky et al. however do not disclose, or suggest, the compounds having the formulae:

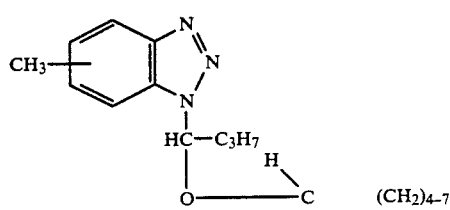

1-(1-cyclo$C_5$-$C_8$alkyloxybutyl)-tolyltriazoles and especially the compound having the formula:

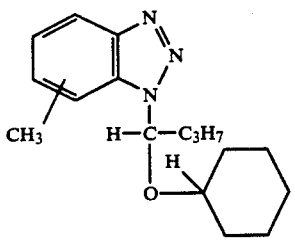

1-(1-cyclohexyloxybutyl)-tolyltriazole. These new compounds represent a further embodiment of the present invention.

Specific examples of compounds of formula I include:
1-(1-methoxyethyl)tolyltriazole
1-(1-methoxpropyl)tolyltriazole
1-(1-isobutoxybutyl)tolyltriazole
1-(1-tert-butoxybutyl)tolyltriazole
1-(1-hexyloxybutyl)tolyltriazole
1-(1-octyloxybutyl)tolyltriazole
1-(1-butoxy-2-methylpropyl)tolyltriazole
1-(1-dodecyloxybutyl)tolyltriazole
1-(1-isopropyloxyethyl)tolyltriazole
1-(1-isopropyloxyethyl)tolyltriazole
1-(1-isopropyloxypropyl)tolyltriazole
1-(1-isopropyloxybutyl)tolyltriazole
1-(1-cyclohexyloxypropyl)tolyltriazole
1-[1-(2-methoxyethoxy)butyl]tolyltriazole
1-[1-(2-ethoxyethoxy)butyl]tolyltriazole The compounds of formula (I) may be produced by the method outlined by Katritzky et al., namely by the acid-catalysed condensation of i) tolyltriazole of formula (III):

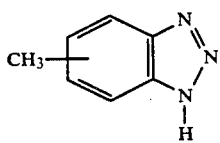

(III)

with ii) an aldehyde of formula R₂CHO (IV) wherein R$_2$ has its previous significance, and with iii) an alcohol of formula R$_3$OH (V) wherein R$_3$ has its previous significance.

The condensation is conveniently effected by heating together, in substantially equimolar amounts, the reactants of formulae (III), (IV) and (V), in a solvent inert to the reactants, while continuously removing an azeotropic mixture of solvent and water formed during the reaction.

Suitable acid catalysts include mineral acids e.g. sulphuric acid; acid clays e.g. bentonite, montmorillonite or Fullers' earth; acid ion-exchange resins e.g. Amberlyst 15; and sulphonic acids e.g. p-toluene sulphonic acid.

The inert solvent used may be cyclohexane, benzene, toluene, xylene or carbon tetrachloride.

The lubricant base of the composition of the present invention may be of mineral oil origin or may be a synthetic material e.g. a carboxylic acid ester, especially those intended for use at temperatures at or above 200° C., or mixtures thereof.

Examples of carboxylic acid ester synthetic lubricants include those based on a diester of a dibasic acid and a monohydric alcohol e.g. dioctyl sebacate or dinonyl adipate; or a triester of trimethylol propane and a monobasic acid or mixture of such acids e.g. trimethylol propane tripelargonate, trimethylol propane tripelargonate, trimethylol propane tricaprylate or mixtures of these; on a tetraester of pentaerythritol and a monobasic acid or a mixture of such acids e.g. pentaerythritol tetracaprylate; or on complex esters derived from monobasic acids, dibasic acids and polyhydric alcohols e.g. a complex ester derived from trimethylolpropane, caprylic acid and sebacic acid; or mixtures of one or more of such carboxylic acid esters.

Other lubricant bases and other synthetic lubricant bases e.g. phosphates, glycols, polyglycols, polyalkylene glycols and poly-alpha olefins are those described e.g. in J.H. Schewe, W. Kobek, "Schmiermittel-Taschenbuch" (Huethig Verlag, Heidelberg 1974), or in D. Klamann, "Schmierstoffe und verwandte Produkte", pages 158 to 174 (Verlag Chemie, Weinheim, 1982).

Mineral oil-based lubricant bases are preferred.

The compositions of the present invention preferably contain 0.01 to 5.0 %, more preferably 0.02 to 1.0 % by weight of at least one compound of formula I, based on the weight of the lubricant base.

In addition to the compound of formula I, the lubricant compositions according to the present invention may contain, in order to improve the operating properties of the lubricant, further additives. Such further additives include e.g. further antioxidants e.g. phenolic antioxidants, amine antioxidants, or other antioxidants, further metal deacti. vators, rust inhibitors, viscosity-index improvers, pour-point depressant, dispersants/surfactants and anti-wear additives.

EXAMPLES OF PHENOLIC ANTIOXIDANTS

1. Alkylated Monophenols 2,6-Di-tert-butyl-4-methylphenol, 2,6-di-tert-butylphenol, 2-tert-butyl-4,6-dimethylphenol, 2,6-di-tert-butyl-4-ethylphenyl, 2,6-di-tert-butyl-4-n-butylphenol, 2,6-di-tert-butyl-4-i-butylphenol, 2,6-di-cyclopentyl-4-methylphenol, 2-(β-methylcyclohexyl)-4,6-di-methylphenol, 2,6-di-octadecyl-4-methylphenol, 2,4,6-tricyclohexylphenol, 2,6-di-tert-butyl-4-methoxymethylphenol, o-tert-butylphenol.

2. Alkylated Hydroquinones 2,6-Di-tert-butyl-4-methoxyphenol, 2,5-di-tert-butylhydroquinone, 2,5-di-tert-amyl-hydroquinone, 2,6-diphenyl-4-octadecyloxyphenol.

3. Hydroxylated Thiodiphenylethers 2,2'-Thio-bis-(6-tert-butyl-4-methylphenol), 2,2'-thio-bis-(4-octylphenol), 4,4'-thio-bis-(6-tert-butyl-3-methylphenol), 4,4'-thio-bis-(6-tert-butyl-2-methylphenol).

4. Alkylidene-Bisphenols 2,2'-Methylene-bis-(6-tert-butyl-4-methylphenol), 2,2'-methylene-bis-(6-tert-butyl-4-ethylphenol), 2,2'-methylene-bis-(4-methyl-6-(α-methylcyclohexyl)-phenol), 2,2'-methylene-bis-(4-methyl-6-cyclo-hexylphenol), 2,2'-methylene-bis-(6-nonyl-4-methylphenol), 2,2'-methylene-bis-(4,6-di-tert-butylphenol), 2,2'-ethylidene-bis-(4,6-di-tert-butylphenol), 2,2'-ethylidene-bis-(6-tert-butyl-4- or -5isobutylphenol), 2,2'-methylene-bis-(6-α-methylbenzyl-4-nonylphenol), 2,2'-methylene-bis-(6-(α,α-dimethylbenzyl)-4-nonylphenyol), 4,4'-methylene-bis-(2,6-di-tert-butylphenol), 4,4'-methylene-bis(6-tert-butyl-2-methylphenol), 1,1'-bis-(5-tert-butyl-4-hydroxy-2-methylphenol)-butane, 2,6-di-(3-tert-butyl-5- methyl-2-hydroxybenzyl)-4-methylphenol, 1,1,3-tris-(5-tert-butyl-4-hydroxy-2-methylphenyl)-3-n-dodecyl)-mercaptobutane; ethyleneglycol-bis-[3,3-bis-(3'-tert-butyl-4'-hydroxyphenyl)-butyrate], bis-(3-tert-butyl-4-hydroxy-5-methylphenyl)-dicyclopentadiene, bis-[2-(3'-tert-butyl-2'-hydroxy-5'-methyl-benzyl)-6-tert-butyl-4-methyl-phenyl]-terephthalate.

5. Benzyl Compounds 1,3,5-Tri-(3,5-di-tert-butyl-4-hydroxybenzyl)-2,4,6-trimethylbenzene, bis-(3,5-di-tert-butyl-4-hydroxybenzyl)-sulfide, 3,5-di-tert-butyl-4-hydroxybenzyl-mercaptoacetic acid-isooctylester, bis-(4-tert-butyl-3-hydroxy-2,6-dimethylbenzyl)-dithiolterephthalate, 1,3,5-tris-(3,5-di-tert-butyl-4-hydroxybenzyl)-isocyanurate, 1,3,5-tris-(4-tert-butyl-3-hydroxy-2,6-dimethylbenzyl)-isocyanurate, 3,5-di-tert-butyl-4-hydroxybenzylphosphonic acid-dioctadecylester, 3,5-di-tert-butyl-4-hydroxybenzyl-phosphonic acid-monoethylester, calcium-salt.

6. Acylaminophenols

4-Hydroxy-lauric acid anilide, 4-hydroxy-stearic acid anilide, 2,4-bis-octylmercapto-6-(3,5-di-tert-butyl-4-hydroxy-anilino)-s-triazine, N-(3,5-di-tert-butyl-4-hydroxyphenyl)-carbamic acid octyl ester.

7. Esters of β-(3,5-di-tert-butyl-4-hydroxyphenol)-propionic acid with mono- or polyhydric alcohols, for example with methanol, diethyleneglycol, octadecanol, triethyleneglycol, 1,6-hexanediol, pentaerythritol, neopentylglycol, tris-hydroxyethylisocyanurate, thiodiethyleneglycol, bis-hydroxyethyl-oxalic acid diamide.

8. Esters of β-(5-tert-butyl-4-hydroxy-3-methylphenyl)-propionic acid with mono- or polyhydric alcohols, for example with methanol, diethyleneglycol, octadecanol, triethyleneglycol, 1,6-hexanediol, pentaerythritol, neopentylglycol, tris-hydroxyethylisocyanurate, thiodiethyleneglycol, di-hydroxyethyl-oxalic acid diamide.

9. Amides of β-(3,5-Di-tert-butyl-4-hydroxyphenyl)-propionic acid for example N,N'-Bis-(3,5-di-tert-butyl-4-hydroxyphenylpropionyl)-hexamet hylenediamine, N,N'-bis-(3,5-di-tert-butyl-4-hydroxyphenyl-propionyl)-trimethylene-diamine, N,N'-bis-(3,5-di-tert-butyl-4-hydroxyphenylpropionyl)-hydrazine.

EXAMPLES OF AMINE ANTIOXIDANTS

N,N'-Di-isopropyl-p-phenylenediamine, N,N'-di-sec.-butyl-p-phenylenediamine, N,N'-bis(1,4-dimethylpentyl)-p-phenylenediamine, N,N'-bis(1-ethyl-3-methyl-pentyl)-p-phenylenediamine, N,N'-bis(1-methyl-heptyl)-p-phenylenediamine, N,N'-dicyclohexyl-p-phenylenediamine, N,N'-diphenyl-p-phenylenediamine, N,N'-di-(naphthyl-2-)-p-phenylendiamine, N-isopropyl-N'-phenyl-p-phenylenediamine, N-(1,3-dimethylbutyl)-N'-phenyl-p-phenylene-diamine, N-(1-methyl-heptyl)-N'-phenyl-p-phenylenediamine, N-cyclohexyl-N'-phenyl-p-phenylenediamine, 4-(p-toluene-sulfonamido)-diphenylamine, N,N'-dimethyl-N,N'-di-sec-butyl-p-phenylenediamine, diphenylamine, N-allyldiphenylamine, 4-isopropoxy-diphenylamine, N-phenyl-1-naphthylamine, N-phenyl-2-naphthylamine, octylated diphenylamine, e.g. p,p'-di-tert-octyldiphenylamine, 4-n-butylaminophenol, 4-butyrylaminophenol, 4-nonanoylamino-phenol, 4-dodecanoylamino-phenol, 4-octadecanoylaminophenol, di-(4-methoxy-phenyl)-amine, 2,6-di-tert-butyl-4-dimethylamino-methylphenol, 2,4'-diamino-diphenylmethane, 4,4'-diamino-diphenylmethane, N,N,N',N'-tetramethyl-4,4'-diamino-diphenylmethane, 1,2-di-(phenylamino)-ethane, 1,2-di-[2-methylphenyl)-amino]-ethane, 1,3-di-(phenylamino)-propane, (o-tolyl)-biguanide, di-[4-(1',3'-dimethylbutyl)-phenyl]amine, tert-octylated N-phenyl-1-naphthylamine, mixture of mono- and dialkylatedtert-butyl-/tert-octyldiphenylamines, 2,3-dihydro-3,3-dimethyl-4H-1,4-benzothiazine, phenothiazine, n-allyl-phenothiazine.

EXAMPLES FOR OTHER ANTIOXIDANTS

Aliphatic or aromatic phosphites, esters of thiodipropionic acid or of thiodiacetic acid, or salts of dithiocarbamic or dithiophosphoric acid.

EXAMPLES OF METAL DEACTIVATORS, FOR EXAMPLE FOR COPPER, ARE

Triazoles, benzotriazoles and derivatives thereof, tolutriazole and derivatives thereof, 2-mercaptobenzothiazole, 2,5-dimercaptothiadiazole, 4,4'-methylene-bis-benzotriazole, 4,5,6,7-tetrahydro-benzotriazole, salicylidenepropylenediamine and salicylamino-guanidine and salts thereof.

EXAMPLES OF RUST INHIBITORS ARE a) Organic acids, their esters, metal salts and anhydrides, e.g. N-oleoyl-sarcosine, sorbitan-mono-oleate, lead-naphthenate, alkenyl-succinic acids and -anhydrides, e.g. dodecenyl-succinic acid anhydride, succinic acid partial esters and amides, 4-nonyl-phenoxy-acetic acid.

b) Nitrogen-containing compounds, e.g. I Primary, secondary or tertiary aliphatic or cycloaliphatic amines and amine-salts of organic and inorganic acids, e.g. oil-soluble alkylammonium carboxylates II Heterocyclic compounds, e.g. substituted imidazolines and oxazolines.

c) Phosphorus-containing compounds, e.g. Amine salts of phosphonic acid or phosphoric acid partial esters, zinc dialkyldithio phasphates.

d) Sulfur-containing compounds, e.g. Barium-dinonylnaphthalene-n-sulfonates, calcium petroleum sulfonates.

EXAMPLES OF VISCOSITY-INDEX IMPROVERS ARE

Polyacrylates, polymethacrylates, vinylpyrrolidone/methacrylate-co-polymers, polyvinylpyrrolidones, polybutenes, olefin-copolymers, styrene/acrylate-copolymers, polyethers.

EXAMPLES OF POUR-POINT DEPRESSANTS ARE

Polymethacrylates, alkylated naphthalene derivatives.

EXAMPLES OF DISPERSANTS/SURFACTANTS ARE

Polybutenylsuccinic acid-amides or -imides, polybutenyl phoshonic acid derivatives, basic magnesium-, calcium-, and barium-sulfonates and -phenolates.

EXAMPLES OF ANTI-WEAR ADDITIVES ARE

Sulfur- and/or phosphorus- and/or halogen-containing compounds e.g. sulfurised vegetable oils, zinc dialkyldithiophosphates, tritolyl-phosphate, chlorinated paraffins, alkyl- and aryldi- and tri-sulfides, triphenylphosphoro. thionate, diethanolaminomethyl-tolutriazole, di(2-ethylhexyl)-aminomethyltolutriazole.

Particularly interesting packages of co-additives are those involving combinations of one or more compounds of formula I together with a phenolic antioxidant e.g. tert.-butylated phenol, or mixture thereof; and/or an amine antioxidant e.g. a di-tert, octyldiphenylamine, especially that produced by the process described in European Patent Specification No. 149422.

The invention also relates to a method of making a lubricant having metal deactivating and/or antioxidant properties, comprising the step of adding to said lubricant an effective amount of a compound of formula I, as described before.

The following Examples further illustrate the present invention. The compounds of Examples 1 and 3 to 5 are new compounds. The compounds are useful as stabilizers in the lubricant compositions of the present invention.

All percentages and parts are by weight, until stated otherwise.

EXAMPLE 1

A mixture of 133 parts tolyltriazole, 79.3 parts n-butyraldehyde, 100.1 parts cyclohexanol and 1.3 parts paratoluene sulphonic acid is heated in 600 parts cyclohexane with simultaneous azeotropic removal of the water formed during the reaction. The reaction is complete after 2 hours. Upon cooling to ambient temperature, the reaction mixture is washed with dilute sodium carbonate solution, then with water and finally dried over anhydrous magnesium sulphate. The dried reaction mixture is filtered and evaporated under reduced pressure and then stripped under vacuum (100° C./4 Pa) to yield 262.9 parts (91.5 %) of 1-(1-cyclohexyloxybutyl) tolyltriazole as a yellow oil. The product is distilled at 175° C./8 Pa to yield a pale yellow oil.

Analysis. $C_{17}H_{25}N_3O$ Requires: C 71.04%, H 8.77%, N 14.62%. Found: C 70.82%, H 9.10%, N 14.56%.

The $^1H$ nmr and infrared spectra are consistent with the structure:

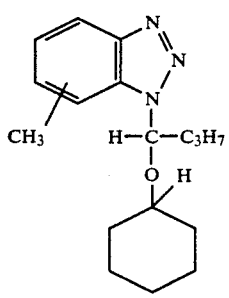

(III)

EXAMPLES 2 to 5

Using the procedure described in Example 1, compounds are prepared having the formulae:

EXAMPLE 2

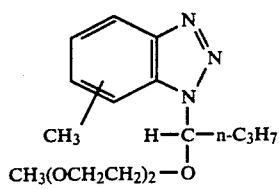

Yield: 76%
bp = 145° C./8 Pa

EXAMPLE 3

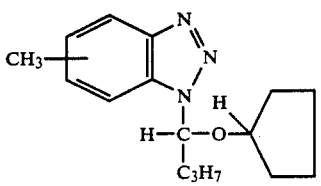

Yield = 80%
bp = 150° C./3 Pa
Analysis $C_{16}H_{23}N_3O$ Requires: C 70.30%; H 8.48%, N 15.37%, Found: C 70.49%, H 8.48%; N 15.79%.

EXAMPLE 4

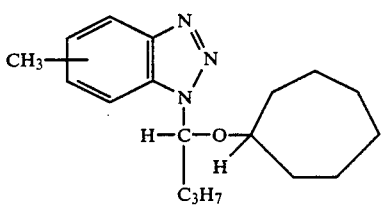

Yield = 76%
bp = 155° C./4 Pa
Analysis: $C_{18}H_{27}N_3O$ Requires: C 71.72%; H 9.03%; N 13.94%; Found: C 71.65%; H 9.43%; N 13.90%.

EXAMPLE 5

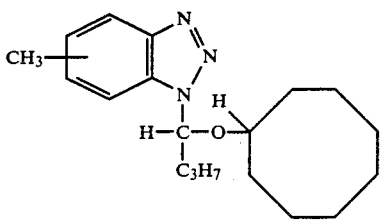

Yield = 89%
bp = 155° C./2 Pa
Analysis: $C_{19}H_{29}N_3O$ Requires: C 72.34%; H 9.27%; N 13.32%; Found: C 72.30%; H 9.60%; N 13.93%.

EXAMPLES 6 to 10

(Modified) ASTM D-130 Copper Strip Test

A 0.05 % solution of the test compound is prepared in a turbine quality mineral oil of viscosity 26.2 mm$^2$/s at 40° C., 4.8 mm$^2$ at 100° C. and S-content of 0.54% in which 50 ppm of elemental sulphur has been dissolved.

A copper strip (60×10×1 mm) is polished with 100 grade silicon carbide grit which has been picked up on cotton wool wetted with petroleum ether. The polished strip is then immediately totally immersed in the prepared solution, which is maintained at 100° C. for 2 hours. After this time, the strip is removed, washed with petroleum ether, dried and its colour is compared with those of the ASTM D-130 Copper Strip Corrosion Standard Chart.

The results are summarised in the following Table:

| Example | Test compound ASTM D-130 Product of Example No. | Rating |
|---|---|---|
| — | Blank (no additive) | 3B |
| 6 | 1 | 1A |
| 7 | 2 | 1A |
| 8 | 3 | 1A |
| 9 | 4 | 1A |
| 10 | 5 | 1A |

A rating of 1 denotes a slight tarnish; a rating of 2 a moderate tarnish; a rating of 3 a dark tarnish; and a rating of 4 severe corrosion. Letters A, B, C and D are used to indicate shadings within the broad numerical values.

The results in the Table demonstrate the excellent test results achieved using compositions according to the present invention.

EXAMPLES 11 to 20

Rotary Bomb Oxidation Test ASTM D-2272

A 0.05% solution of the test compound is prepared in a turbine quality mineral oil of viscosity 26.2 mm$^2$/s at 40° C., 4.8 mm$^2$/s at 100° C. and S-content of 0.54 % which also contains either a phenolic or aminic antioxidant, or both.

The time taken for the oxygen pressure in the bomb to drop more than 175 kPa below the maximum pressure is recorded.

The results obtained are set out in the following Table:

| Example | Product of Example No. | Antioxidant A | Antioxidant B | RBOT mins to 175 kPA pressure drop |
|---|---|---|---|---|
| — | (Base oil alone) | — | — | 25 mins |
| — | — | 0.10% | — | 65 mins |
| — | — | — | 0.10% | 85 mins |
| 11 | 1 | 0.10% | — | 300 mins |
| 12 | 1 | — | 0.10% | 350 mins |
| 13 | 2 | — | 0.10% | 240 mins |
| 14 | 1 | 0.10% | 0.10% | 430 mins |
| 15 | 3 | 0.10% | — | 360 mins |
| 16 | 3 | — | 0.10% | 310 mins |
| 17 | 4 | 0.10% | — | 350 mins |
| 18 | 4 | — | 0.10% | 290 mins |
| 19 | 5 | 0.10% | — | 335 mins |
| 20 | 5 | — | 0.10% | 370 mins |

Antioxidant A is a commercially available mixture of tert-butylated phenols.

Antioxidant B is a commercially available di-tert-octylated diphenylamine.

The results in the Table indicate that when used in combination with a further amine or phenolic antioxidant, the stabilisers of formula I impart synergistic antioxidant properties to the lubricant compositions of the invention.

What is claimed is:

1. Lubricant compositions comprising a lubricant base and, as metal deactivator and antioxidant, an effective amount of at least one compound having the formula (I):

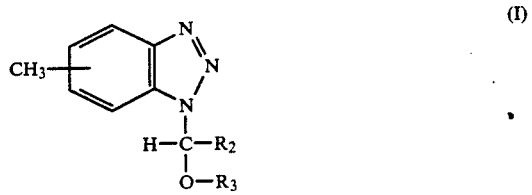

wherein
  $R_2$ is $C_1-C_{12}$ straight or branched chain alkyl; and
  $R_3$ is $C_1-C_{12}$ straight or branched chain alkyl interrupted by one or more O-atoms or $R_3$ is $C_5-C_{12}$ cycloalkyl.

2. Lubricant compositions according to claim 1 wherein $R_2$ is $C_1-C_4$alkyl; and $R_3$ is $C_1-C_5$alkyl interrupted by one or two O-atoms, or is $C_5-C_8$cycloalkyl.

3. Lubricant compositions according to claim 1 wherein $R_2$ is i- or n-propyl and $R_3$ is a group of formula $(CH_2CH_2O)_2CH_3$ or is $C_5-C_8$cycloalkyl.

4. Lubricant compositions according to claim 1 wherein the lubricant base is a carboxylic acid ester or the lubricant base is of mineral oil origin.

5. Lubricant compositions according to claim 1 wherein the amount of the compound of formula I present ranges from 0.01 to 5% by weight, based on the weight of the lubricant base.

6. Lubricant compositions according to claim 5 wherein the amount of the compound of formula I present ranges from 0.02 to 1.0% by weight, based on the weight of the lubricant base.

7. Lubricant compositions according to claim 1 wherein the compositions also include one or more of a further anti-oxidant, a further metal deactivator, a rust inhibitor, a viscosity-index improver, a pour-point depressant, a dispersant/surfactant and an anti-wear additive.

8. Lubricant compositions according to claim 7 wherein the further antioxidant is an amine antioxidant or a phenolic antioxidant or a mixture of both.

9. Lubricant compositions according to claim 8 wherein the phenolic antioxidant is one or more tert.-butylated phenols.

10. Lubricant compositions according to claim 8 wherein the amine antioxidant is one or more di-tert.-octylated diphenylamines.

* * * * *